United States Patent [19]

Hughes et al.

[11] 4,126,577

[45] Nov. 21, 1978

[54] METAL COMPLEX

[75] Inventors: William B. Hughes; Ernest A. Zuech, both of Bartlesville, Okla.

[73] Assignee: Phillips Petroleum Company, Bartlesville, Okla.

[21] Appl. No.: 501,582

[22] Filed: Aug. 29, 1974

Related U.S. Application Data

[60] Continuation of Ser. No. 274,727, Jul. 24, 1972, abandoned, which is a division of Ser. No. 80,230, Oct. 12, 1970, Pat. No. 3,691,253, which is a division of Ser. No. 694,875, Jan. 2, 1968, Pat. No. 3,562,178, which is a continuation-in-part of Ser. No. 635,656, May 3, 1967, abandoned.

[51] Int. Cl.$^2$ .................. B01J 23/20; B01J 23/22; B01J 31/18
[52] U.S. Cl. .................................................. 252/431 N
[58] Field of Search .................... 423/386; 260/429 R, 260/329 MF; 252/431 N

[56] References Cited

U.S. PATENT DOCUMENTS

| | | | |
|---|---|---|---|
| 3,294,828 | 12/1966 | Werner | 252/431 N |
| 3,475,471 | 10/1969 | Maxfield | 260/429 R |

*Primary Examiner*—Allen B. Curtis

[57] ABSTRACT

A compound of vanadium or niobium complexed with NO and a selected complexing agent.

18 Claims, No Drawings

METAL COMPLEX

This application is a continuation of copending application Ser. No. 274,727, filed July 24, 1972, now abandoned which is a divisional application of Ser. No. 80,230, filed Oct. 12, 1970, now U.S. Pat. No. 3,691,253, issued Sept. 12, 1972, which is a divisional of copending application Ser. No. 694,875, filed Jan. 2, 1968, now U.S. Pat. No. 3,562,178 issued Feb. 9, 1971, which is a continuation-in-part of application Ser. No. 635,656, filed May 3, 1967, now abandoned.

This invention relates to the conversion of olefin hydrocarbons and to a homogeneous catalyst for such conversion. In one aspect, this invention relates to the olefin reaction. In another aspect, it relates to the conversion of olefins to other olefins having different molecular weights. In still another aspect, it relates to a homogeneous catalyst.

The term "olefin reaction", as used herein, is defined as a process for the catalytic conversion in the presence of a catalyst of a feed comprising one or more ethylenically unsaturated compounds to produce a resulting product which contains at least 10 percent by weight of product compounds, which product compounds can be visualized as resulting from at least one primary reaction, as defined below, or the combination of at least one primary reaction and at least one unsaturated bond isomerization reaction, and wherein the sum of the compounds contained in said resulting product consisting of hydrogen, saturated hydrocarbons, and compounds which can be visualized as formed by skeletal isomerization but which cannot be visualized as formed by one or more of the above-noted reactions, comprises less than 25 percent by weight of the total of said resulting product. Feed components and unsaturated bond isomers thereof are not included in the resulting product for the purpose of determining the above-noted percentages.

In the olefin reaction, as defined above, the primary reaction is a reaction which can be visualized as comprising the breaking of two existing unsaturated bonds between first and second carbon atoms and between third and fourth carbon atoms, respectively, and the formation of two new unsaturated bonds. Said first and second carbon atoms and said third and fourth carbon atoms can be in the same or different molecules.

The olefin reaction according to this invention is illustrated by the following reactions:

(1) The disproportionation of an acyclic mono- or polyene having at least three carbon atoms into other acyclic mono- or polyenes of both higher and lower number of carbon atoms; for example, the disproportionation of propylene yields ethylene and butenes; the disproportionation of 1,5-hexadiene yields ethylene and 1,5,9-decatriene;

(2) The conversion of an acyclic mono- or polyene having three or more carbon atoms and a different acyclic mono- or polyene having three or more carbon atoms to produce different acyclic olefins; for example, the conversion of propylene and isobutylene yields ethylene and isopentene;

(3) The conversion of ethylene and an internal acyclic mono- or polyene having four or more carbon atoms to produce other olefins having a lower number of carbon atoms than that of the acyclic mono- or polyene; for example, the conversion of ethylene and 4-methylpentene-2 yields 3-methylbutene-1 and propylene;

(4) The conversion of ethylene or an acyclic mono- or polyene having three or more carbon atoms and a cyclic mono- or cyclic polyene to produce an acyclic polyene having a higher number of carbon atoms than that of any of the starting materials; for example, the conversion of cyclooctene and 2-pentene yields 2,10-tridecadiene; the conversion of 1,5-cyclooctadiene and ethylene yields 1,5,9-decatriene;

(5) The conversion of one or more cyclic mono- or cyclic polyenes to produce a cyclic polyene having a higher number of carbon atoms than any of the starting materials; for example, the conversion of cyclopentene yields 1,6-cyclodecadiene and continued reaction can produce higher molecular weight materials;

(6) The conversion of an acyclic polyene having at least seven carbon atoms and having at least five carbon atoms between any two double bonds to acyclic and cyclic mono- and polyenes having a lower number of carbon atoms than that of the feed; for example, the conversion of 1,7-octadiene yields cyclohexene and ethylene; or (7) The conversion of one or more acyclic polyenes having at least three carbon atoms between any two double bonds to produce acyclic and cyclic mono- and polyenes generally having both a higher and lower number of carbon atoms than that of the feed material; for example, the conversion of 1,4-pentadiene yields 1,4-cyclohexadiene and ethylene.

New catalytic processes have been discovered in recent years for the conversion of olefins to other olefin products, including products of both higher and lower molecular weights whereby olefins of relatively low value are converted to olefins of increased value. Such conversions have heretofore been carried out using heterogeneous catalysts comprising compounds such as compounds of molybdenum or tungsten and generally associated with solid materials such as alumina or silica. It has now been found that these olefin conversions can be carried out in a substantially homogeneous state using, as catalysts, selected coordination complexes of niobium or vanadium in combination with aluminum-containing catalytic adjuvants to produce olefins of increased value including solid products, for example, rubber suitable for the manufacture of tires, wire coating, footwear and other industrial products.

It is an object of this invention to provide a method and a catalyst for the conversion of olefin hydrocarbons. It is also an object of this invention to provide a catalyst for the conversion of olefin hydrocarbons. A further object is to provide a homogeneous catalyst for the olefin reaction. Still another object is to provide a method for converting olefins to other olefins of higher and lower number of carbon atoms utilizing a homogeneous catalyst. The provisions of a homogeneous catalyst for converting olefins to other olefins of higher and lower number of carbon atoms is yet another object of the invention. Other aspects, objects and advantages of the invention will be apparent to one skilled in the art upon study of the disclosure, including the detailed description of the invention.

According to the process of the invention, cyclic olefins, acyclic olefins, and mixtures of these, including mixtures with ethylene, are converted to other olefins by contact with a catalyst system, which forms on admixing, under catalyst formation conditions, components comprising (a) metal complex represented by the formula $[(L)_a(NO)_bM_cZ_d]_x$ wherein M is niobium or vanadium; each Z is a halogen, or a CN, SCN, OCN, or $SnCl_3$ radical; each (L) is selected from $R_3QO$, O, CO, $[(RCO)_2CH]$-, R—S—R, $(R_2NCSS\text{―})$ $R^5(CN)_b$, $R^5(COO\text{―})_b$, $(R^5COR^2COO\text{―})$, $$\underset{R^3\diagup S}{\frown}$$

$(\underline{CHR^4}\underline{=CR^4}\underline{=CH_2}\text{―})$; $a$ is 1–6, $b$ is 1–2, $c$ is 1–4, $d$ is 0–6, and the number of Z, (L), and NO groups in the complex is not greater than the number required for the metal to achieve the closed shell electronic configuration of the next higher number inert gas; $x$ is a number indicative of the polymeric state of the complex; R is an aromatic or saturated aliphatic hydrocarbon radical, including radicals which are substituted with groups which do not adversely effect the performance of the finished catalyst such as alkoxy and halo groups, having up to 20 carbon atoms; $R^2$ is a divalent R radical; $R^5$ is an aromatic, saturated aliphatic, or ethylenically unsaturated aliphatic radical having up to 30 carbon atoms; $R^3$ is a divalent saturated or ethylenically unsaturated aliphatic radical having from 4 to 10 carbon atoms; $R^4$ is hydrogen or a methyl radical; and Q is phosphorus, arsenic or antimony; with (b) an aluminum-containing catalytic adjuvant selected from (1) $R_eAlX_f$, or (2) a mixture of (1) compounds, or (3) a mixture of one or more $R_eAlX_f$ or $AlX_3$ compounds with one or more compounds represented by $R'_gM'X_h$, wherein R is an aromatic or saturated aliphatic hydrocarbon radical having up to 20 carbon atoms, including alkoxy and halo derivatives thereof, preferably an alkyl radical having up to 10 carbon atoms; R' is hydrogen or R; X is halogen; M' is a metal of Group IA, IIA or IIIA; $e$ is an integer from 1 to 3; $f$ is 0 or an integer from 1 to 2, the sum of $e$ and $f$ being 3; $g$ is an integer from 1 to 3; and $h$ is 0 or an integer from 1 to 2, the sum of $g$ and $h$ being equal to the valence of M'. When the adjuvant is (1) and acyclic olefins are converted, $f$ is preferably 1 or 2.

The Group IA, IIA and IIIA metals are those of the Periodic Table of Elements appearing in Handbook of Chemistry and Physics, Chemical Rubber Company, 45th edition (1964).

Some examples of compounds of (1) and (2) are methylaluminum dichloride, dimethylaluminum chloride, methylaluminum sesquichloride, ethylaluminum dichloride, ethylaluminum sesquichloride, di(2-ethylhexyl) aluminum bromide, phenylaluminum dichloride, di(3-ethoxypropyl) aluminum bromide, benzylaluminum dibromide, dieicosylaluminum bromide, and the like, and mixtures thereof.

Some examples of the $R'_gM'X_h$ compounds of (3) are phenyllithium, methylsodium, lithium hydride, lithium aluminum hydride, lithium borohydride, diethylzinc, dipropylzinc, triethylaluminum, trieicosylaluminum, di(12-chlorododecyl)aluminum chloride, and the like, and mixtures thereof. Preferred (b) components of the catalyst system are the (1) or (2) adjuvants.

Among the suitable metal complexes are those represented by the formula $[(L)_a(NO)_bM_cZ_d]_x$ wherein M is niobium or vanadium; each Z is a halogen, CN, SCN, OCN, or $SnCl_3$ radical; each (L) is a ligand represented by the formula $R_3QO$, O, $[(RCO_2)_2CH\text{―}]$, R—S—R, $R^5(CN)_b$, $R^5(COO\text{―})_b$, $(R^5COR^2COO\text{―})$, $$\underset{R^3\diagup S}{\frown},$$

or $(\underline{CHR^4}\underline{=CR^4}\underline{=CH_2}\text{―})$; $a$, $b$, $c$, and $d$ are integers wherein $a$ is 1–6, $b$ is 1–2, $c$ is 1–4, $d$ is 0–6, and the number of Z, (L), and NO groups in the complex is not greater than the number required for the metal to achieve the closed shell electronic configuration of the next higher atomic number inert gas; $x$ is the number of the polymeric state of the complex; R is an aromatic or saturated aliphatic hydrocarbon radical having up to 20 carbon atoms per molecule including alkoxy and halo derivatives thereof; $R^2$ is a divalent R radical; $R^3$ is a divalent saturated or ethylenically unsaturated aliphatic radical having from 4 to 10 carbon atoms; $R^4$ is hydrogen or a methyl radical; and $R^5$ is an aromatic, saturated aliphatic, or ethylenically unsaturated aliphatic radical having up to 30 carbon atoms.

The metal complex can consist essentially of (A) niobium or vanadium compound which is niobium or vanadium halide, oxyhalide, cyanide, thiocyanate, cyanate, trichlorostannate, or salt of a hydrocarbon organic acid having up to 30 carbon atoms per molecule, (B) NO or a nitrosyl halide, and (C) one or more complexing agents capable of complexing with said niobium or vanadium, wherein said complexing agent is represented by the formula: $RCOCH_2COR$; $R^5(CN)_b$; R—S—R;

$$\underset{R^3\diagup S}{\frown};$$

acids of the formula $R^5(COOH)_b$; or ketoacids of the formula $R^5COR^2COOH$; wherein R is an aromatic or saturated aliphatic hydrocarbon radical having up to 20 carbon atoms including alkoxy and halo derivatives thereof; $R^2$ is a divalent R radical, $R^3$ is a divalent saturated or ethylenically unsaturated aliphatic radical having 4 to 10 carbon atoms, $R^5$ is an aromatic, saturated aliphatic, or ethylenically unsaturated aliphatic radical having up to 30 carbon atoms, and $b$ is an integer of 1 or 2.

Metal complex (a) compounds can also be the products formed by the admixture, under complex forming conditions, of a suitable niobium or vanadium compound such as, for example, a halide, oxyhalide, carbonyl, or salt of an organic acid having up to 30 carbon atoms per molecule, or inorganic acid with NO or a nitrosyl halide and with one or more complexing agents selected from $R_3QO$, $RCOCH_2COR$, $R^5(CN)_b$, R—S—R, $$\underset{R^3\diagup S}{\frown},$$

and compounds containing the radicals $(R_2NCSS\text{―})$, $R^5(COO\text{―})$, $(R^5COR^2COO\text{―})$, or $(\underline{CHR^4}\underline{=CR^4}\underline{=CH_2}\text{―})$; wherein Q, R, $R^2$, $R^3$, $R^4$, $R^5$, and $b$ are as previously defined.

The invention also includes a process for preparing a metal complex which comprises admixing under complexing conditions and in complex forming ratios a niobium or vanadium compound which is niobium or vanadium halides, oxyhalide, cyanide, thiocyanate, cyanate, trichlorostannate, or salt of a hydrocarbon acid having up to 80 carbon atoms per molecule, with NO or a nitrosyl halide, and with at least one complexing agent capable of complexing said niobium or vanadium wherein said complexing agent is represented by the formula: $RCOCH_2COR$; $R^5(CN)_b$; R—S—R;

acids of the formula $R^5(COOH)_b$; or ketoacids of the formula $R^5COR^2COOH$; wherein R is an aromatic or saturated aliphatic hydrocarbon radical having up to 20 carbon atoms including alkoxy and halo derivatives thereof; $R^2$ is a divalent R radical, $R^3$ is a divalent saturated or ethylenically unsaturated aliphatic radical having 4 to 10 carbon atoms, $R^5$ is an aromatic, saturated aliphatic, or ethylenically unsaturated aliphatic radical having up to 30 carbon atoms, and b is an integer of 1 or 2.

Some examples of suitable niobium or vanadium starting compounds are:

| | |
|---|---|
| $NbBr_5$ | $VF_3$ |
| $NbCl_5$ | $VF_5$ |
| $NbF_5$ | $VOCl$ |
| $NbOBr_3$ | $VOBr$ |
| $NbOCl_3$ | $VOBr_2$ |
| $VBr_3$ | $VOBr_3$ |
| $VCl_2$ | $VO_2Cl$ |
| $VCl_3$ | $VOCl_2$ |
| $VCl_4$ | $VOCl_3$ | and the like, and mixtures thereof.

An exemplary group of niobium or vanadium starting compounds includes the niobium or vanadium halides and oxyhalides.

Some examples of suitable complexing agents for the preparation of the metal (a) components of the catalyst system of the present invention are:

| | |
|---|---|
| triphenylphosphine oxide | phenylacetic acid |
| tribenzylphosphine oxide | oxalic acid |
| trimethylarsine oxide | malonic acid |
| tributylstibine oxide | acetoacetic acid |
| tricyclopentylarsine oxide | benzoylacetic acid |
| tricyclohexylphosphine oxide | β-acetylpropionic acid |
| trieicosylstibine oxide | δ-acetobutyric acid |
| tridecylphosphine oxide | acetonitrile |
| tri-p-tolyphosphine oxide | butyronitrile |
| acetic acid | 1,2-cyclohexylenedinitrile |
| propionic acid | ethylenedinitrile |
| butanoic acid | acrylonitrile |
| 2-methylpropionic acid | 2,4-pentanedione |
| pentanoic acid | 1,3-diphenyl-1,3-pentanedione |
| hexanoic acid | 3,5-heptanedione |
| octanoic acid | 4-cyclohexyl-2,4-butanedione |
| dodecanoic acid | ethylsulfide |
| hexadecanoic acid | phenylsulfide |
| octadecanoic acid | methylethyl sulfide |
| triacontanoic acid | thiophene |
| benzoic acid | tetrahydrothiophene |
| | sodium diethyldithiocarbamate |
| | potassium dimethyldithiocarbamate |

Examples of suitable complexing agents for the preparation of the metal (a) components of the catalyst system of the present invention also are represented by the group wherein said complexing agent is triphenylphosphine oxide, tribenzylphosphine oxide, trimethylarsine oxide, tributylstibine oxide, tricyclopentylarsine oxide, tricyclohexylphosphine oxide, trieicosylstibine oxide, tridecylphosphine oxide, tri-p-tolylphosphine oxide, acetic acid, propionic acid, butanoic acid, 2-methylpropionic acid, pentanoic acid, hexanoic acid, octanoic acid, dodecanoic acid, hexadecanoic acid, octadecanoic acid, triacontanoic acid, benzoic acid, phenylacetic acid, oxalic acid, malonic acid, acetoacetic acid, benzoylacetic acid, β-acetylpropionic acid, γ-acetobutyric acid, acetonitrile, butyronitrile, 1,2-cyclohexylenedinitrile, ethylenedinitrile, acrylonitrile, 2,4-pentanedione, 1,3-diphenyl-1,3-pentanedione, 3,5-heptanedione, 4-cyclohexyl-2,4-butanedione, ethylsulfide, phenylsulfide, methylethyl sulfide, thiophene, or tetrahydrothiophene.

Some examples of metal complex (a) components are:

NO-treated benzoic acid-treated $NbCl_5$
NO-treated (tetrahydrothiophene)$NbBr_5$
NO-treated (tetrahydrothiophene)$NbCl_5$
NO-treated (dimethyldithiocarbamate)$_4Nb$
NOBr-treated (ethylenedinitrile)$O_2V_2$(acetate)$_4$
NOCl-treated VO(lactate)$_2$
NOI-treated (2,4-pentanedionate)$_2O_2V$
NOCl-treated (2,4-pentanedionate)$_2$(triphenylphosphine oxide)V
NOBr-treated (1-phenyl-1,3-butanedionate)$_2V$
NO-treated (2,4-pentanedionate)$OVCl_2$
NO-treated (acetate)$_2VCl_4$
NOCl-treated ($\pi$-allyl)$_3V$
NOCl-treated (2,4-pentanedionate)$_3V$
NOBr-treated (1-phenyl-1,3-butanedionate)$_3V$
(NO)V(CO)$_5$ and the like, and mixtures thereof.

Examples of vanadium complexes include:

NOBr-treated (ethylenedinitrile)$O_2V_2$(acetate)$_4$
NOCl-treated VO(lactate)$_2$
NOI-treated (2,4-pentanedionate)$_2O_2V$
NOCl-treated (2,4-pentanedionate)$_2$(triphenylphosphine oxide)V
NOBr-treated (1-phenyl-1,3-butanedionate)$_2V$
NO-treated (2,4-pentanedionate)$OVCl_2$
NO-treated (acetate)$_2VCl_4$
NOCl-treated ($\pi$-allyl)$_3V$
NOCl-treated (2,4-pentanedionate)$_3V$ and
NOBr-treated (1-phenyl-1,3-butanedionate)$_3V$ Examples of niobium metal complexes include:

NO-treated benzoic acid-treated $NbCl_5$
NO-treated (tetrahydrothiophene)$NbBr_5$
NO-treated (tetrahydrothiophene)$NbCl_5$ The formula $[(L)_a(NO)_bM_cZ_d]_x$ is used herein to identify the product obtained by the admixture, under catalyst forming conditions, of the metal compound with one or more ligand-forming materials whether or not the components are present in the complex as indicated in the formula.

When the (a) component of the catalyst system is the product obtained by combining a niobium or vanadium compound with NO or a nitrosyl halide and with one or more ligand-forming materials, the molar proportion of transition metal salt to the selected ligand-former is preferably in the broad range of from about 0.1:1 to about 10:1, more preferably about 0.2:1 to 2:1. The products are obtained by combining these ingredients at any convenient temperature, however, excessively high temperatures at which some of the components tend to decompose or excessively low temperatures at which some of the components tend to crystallize or otherwise tend to become unreactive, should be avoided. Generally, it will be preferred to combine the components at a temperature in the range of from about $-25°$ to about 130° C., more preferably 0° to about 60° C., for a time in the range of from a few seconds up to about 24 hours, preferably in the presence of a diluent in which the components of the reaction are at least partially soluble. Any convenient diluent such as carbon tetrachloride, methylene chloride, benzene, cyclohexane, xylene, isooctane, chlorobenzene, and the like, can be used for this purpose. Any order of addition can be used. Such reaction product mixtures need not be isolated but can be used directly in the formation of the catalyst system. In general, the (a) component is fully prepared before contact is made with the (b) component or adjuvant.

The above-described (b) and (a) components of the catalyst system are generally combined, for use in this invention, in proportions in the range of from about 0.1:1 to about 20:1, preferably from about 1:1 to about 10:1 mols of the (b) component to mols of the (a) component. The catalyst is prepared simply by combining these catalyst components under conditions of time and temperature which permit the catalytically active reagent reaction product to form. This combination occurs very readily and, in general, the components can be mixed at any convenient temperature, avoiding excessively high or low temperatures as stated above, within the range of from about −80° to about 100° C., preferably 0°–60° C., for a few seconds or for periods up to several hours in the presence of a diluent in which both the components are at least partially soluble. Any convenient diluent such as benzene, xylene, cyclohexane, chlorobenzene, methylene chloride, ethylene dichloride, and the like, can be used for this purpose. Halogenated diluents are generally preferred. The mixing of these two catalyst components is generally carried out in the substantial absence of air or moisture, generally in an inert atmosphere. After the catalytic mixture is formed, it need not be isolated but can be added directly to the reaction zone as a solution in its preparation solvent. If desired, the catalyst components can be separately added, in any order, to the reaction zone either in the presence or absence of the feed olefin.

Olefins applicable for use in the process of the invention are nontertiary, nonconjugated, acyclic mono- or polyenes having at least 3 carbon atoms per molecule including cycloalkyl, cycloalkenyl and aryl derivatives thereof; cyclic mono- and polyenes having at least 4 carbon atoms per molecule including alkyl and aryl derivatives thereof, mixtures of the above olefins; and mixtures of ethylene and the above olefins. Many useful reactions are accomplished with such cyclic olefins having 4–30 carbon atoms per molecule. Nontertiary olefins are those wherein each carbon atom, which is attached to another carbon atoms by means of a double bond, is also attached to a hydrogen atom.

Some specific examples of acyclic olefins suitable for reactions of this invention include propylene, 1-butene, 2-butene, 1-pentene, 2-pentene, 1-hexene, 1,4-hexadiene, 2-heptene, 4-methyl-2-octene, 1-octene, 2,5-octadiene, 2-nonene, 1-dodecene, 2-tetradecene, 1-hexadecene, 1-phenylbutene-2, 4-octene, 3-eicosene, 3-hexene, 1,4-pentadiene, 1,4,7-dodecatriene, 4-methyl-4-octene, 4-vinylcyclohexene, 1,7-octadiene, 1,5-eicosadiene, 2-triacontene, 2,6-dodecadiene, 1,4,7,10,13-octadecapentaene, 8-cyclopentyl-4,5-dimethyl-1-decene, 6,6-dimethyl-1,4-octadiene, and 3-heptene, and the like, and mixtures thereof.

Some specific examples of cyclic olefins suitable for the reactions of this invention are cyclobutene, cyclopentene, cycloheptene, cyclooctene, 5-n-propylcyclooctene, cyclodecene, cyclododecene, 5,5,4,4-tetramethylcyclononene, 3,4,5,6,7-pentaethylcyclodecene, 1,5-cyclooctadiene, 1,5,9-cyclododecatriene, 1,4,7,10-cyclododecatetraene, 6-methyl-6-ethyl-cyclooctadiene-1,4, and the like, and mixtures thereof.

It will be understood by those skilled in the art that not all olefinic materials will be converted by the present invention with equal effectiveness. The reactions described in the present invention are equilibrium-limited reactions and, barring the selective removal of one or more products from the reaction zone, the extent of conversion will depend upon the thermodynamics of the specification system observed. Thus, conversion of olefinic materials to give specific products can be thermodynamically favored while the reverse reaction is very slow and ineffective. For example, 1,7-octatriene is converted to equilibrium-favored products such as cyclohexene and ethylene. The reverse reaction of ethylene and cyclohexene, correspondingly, goes very poorly. Other well known factors, such as steric hindrance in bulky molecules, significantly and sometimes drastically affect the rates of reaction of some olefins such that extremely long reaction times are required.

The reaction of symmetrical monoolefins with themselves, to give different olefin products, will sometimes proceed very slowly, requiring some double bond migration to take place before the reaction will proceed at a significant rate. For the same reason, the conversion of a mixture of ethylene and a 1-olefin for example can be more difficult than the conversion of ethylene with an internal olefin, some double bond isomerization also being required in this instance.

It has also been found that branching also retards the olefin reactivity in proportion to its propinquity to the reacting double bond. Analogously, the presence of inert polar substituents on the olefinic compound appears tolerable only if located some distance from the double bond.

Thus, the present invention is directed primarily to the conversion of those olefins or combination of olefins which are capable of undergoing the olefin reaction to a significant degree when contacted with the catalyst of the present invention under reaction conditions suitable for effecting the olefin reaction.

Presently preferred olefinic feed compounds are those contained in the following classes:

(1) Acyclic monoolefins, including those with aryl, cycloalkyl, and cycloalkenyl substituents, having 3–20 carbon atoms per molecule with no branching closer than about the 3- position and no quaternary carbon atoms or aromatic substitution closer than the 4- position to the double bond, and mixtures of such unsubstituted acyclic monoolefins. Some examples of these are: propylene, pentene-1, pentene-2, butene-1, butene-2, 3-methylbutene-1, hexene-2, octene-4, nonene2, 4-methylpentene-1, decene-3, 8-ethyldecene-2, dodecene-4, vinylcyclohexane, 4-vinylcyclohexene, eicosene-1, and the like.

(2) A mixture of ethylene and one or more acyclic unsubstituted internal monoolefins of (1). Some examples of such mixtures are: ethylene and butene-2, ethylene and pentene-2, ethylene and hexene-3, ethylene and heptene-3, ethylene and 4-methylpentene-2, ethylene and octene-4, ethylene and dodecene-4, and the like.

(3) Acyclic, nonconjugated polyenes having from 5 to about 20 carbon atoms per molecule, containing from 2 to about 4 double bonds per molecule and having at least one double bond with no branching nearer than the 3- position and no quaternary carbon atom nearer than the 4- position to that double bond, or mixtures of such polyenes. Some examples are: 1,4-pentadiene, 1,5-hexadiene, 1,7-octadiene, 2,6-decadiene, 1,5,9-dodecatriene, 4-methylheptadiene-1,6,1,7-octadiene, 1,6-octadiene, and the like.

(4) A mixture of ethylene and one or more acyclic polyenes of (3) which contain at least one internal double bond. Some examples are: ethylene and 1,6-octadiene, ethylene and 1,5-decadiene, and the like.

(5) Cyclopentene.

(6) Monocyclic and bicyclic monoolefins having 7 to 12 ring carbon atoms, including those substituted with up to 3 alkyl groups having up to about 5 carbon atoms, with no branching closer than the 3- position and with no quaternary carbon atoms closer than the 4- position to that double bond, and mixtures of such olefins including mixtures with cyclopentene. Some examples are: cycloheptene, cyclooctene, 4-methylcyclooctene, 3-methyl-5-ethylcyclodecene, cyclononene, cyclododecene, norbornene, and the like.

(7) A mixture of one or more of the monocyclic olefins of (6) with either ethylene or with one or more unsubstituted acyclic monoolefins of (1). Some examples of these are: ethylene and cycloheptene, ethylene and cyclooctene, propylene and cyclodecene, pentene-2 and cyclooctene, ethylene and cyclododecene, and the like.

(8) Monocyclic and bicyclic nonconjugated polyenes having from 5 to about 12 ring carbon atoms, including those substituted with up to 3 alkyl groups having up to about 5 carbon atoms each, having at least one double bond with no branching closer than the 3- position and with no quaternary carbon atoms closer than the 4- position to that double bond, and mixtures thereof. Some examples of these are: 1,5-cyclooctadiene, 1,5,9-cyclododecatriene, 1,4-cycloheptadiene, norbornadiene, and the like.

(9) A mixture of one or more monocyclic polyenes of (8) with one or more acyclic 1-olefins having from 2 to about 10 carbon atoms, having no branching nearer than the 3- position and no quaternary carbon atoms nearer than the 4- position to the double bond. Some examples of these are: 1,5-cyclooctadiene and ethylene, 1,5,9-cyclododecatriene and ethylene, 1,5,9-cyclododecatriene and pentene-1, and the like.

(10) Polar group-substituted olefinic compounds of classes (1) through (9) containing from about 5 to about 20 carbon atoms per molecule in which the polar group, such as halogen atom, is sufficiently removed from the active double bond (generally, no nearer to the double bond than the 5-position) so as not to interfere with the reaction, and mixtures with unsubstituted members of class (1). Some examples are: 5-chloropentene-1, a mixture of pentene-2 and 5-chloropentene-1, and the like.

According to the process of the invention, the conversion of the olefin or mixture of olefins can take place at any convenient temperature in the broad range of −30° to about 150° C., preferably 0° to 75° C. The conversion can be carried out at any convenient pressure which is sufficient to maintain a liquid phase within the reaction zone. A diluent such as that used in the catalyst preparation or another inert solvent can be used in the reaction if desired. In general, any inert diluent which will maintain a substantially homogeneous reaction phase can be used. The time of contact will depend upon the desired degree of conversion with the specific feed olefins and the specific catalysts used but will, generally, be in the range of from about 0.1 minute to about 20 hours, preferably 5 to 120 minutes. The proportion of the catalyst composition to olefin feed in the reaction zone will generally be in the range of about 0.001–100 millimoles of niobium or vanadium per mole of olefin feed.

Any conventional contacting technique can be utilized for the olefin conversion and batchwise or continuous operation can be utilized. After the reaction period, the products can be separated and/or isolated by conventional means such as by fractionation, crystallization, adsorption, and the like. Unconverted feed materials or products not in the desired molecular weight range can be recycled. If desired, the catalyst can be destroyed by treatment with sufficient water or alcohol to deactivate the catalyst prior to the separation of the products. In some cases, the catalyst which is separated from the products can be recycled to the reaction zone for additional use.

The invention can be further illustrated by the following example.

EXAMPLE

An 0.81 g (0.003 mole) quantity of NbCl$_5$ was mixed with 30 ml of chlorobenzene and 0.73 g of benzoic acid in a nitrogen-purged 7-ounce reaction bottle. The contents of the bottle were then treated with gaseous NO at 25 psig for 1 hour at room temperature. The reactor was vented, evacuated, and flushed with nitrogen. A 5 ml portion of the above mixture was then mixed with 5 ml chlorobenzene, 0.5 ml methylaluminum sesquichloride, and 10 ml pentene-2 in a dry nitrogen purged 7-ounce reaction bottle and the mixture was allowed to react at room temperature, with stirring, for 30 minutes.

A sample of the reaction mixture was analyzed by gas-liquid chromatography, and the olefin content was found to be as follows, in weight percent:

| | |
|---|---|
| Butenes | 1.7 |
| Pentenes | 96.3 |
| Hexenes | 2.1 |

Some heavier polymeric material was also obtained.

In the practice of the process of this invention, the feed olefins, catalysts and operating conditions disclosed include combinations wherein solid, rubbery materials are produced; for example, if a propylene feed and a suitable aluminum-containing adjuvant such as methylaluminum sesquihalide or methylaluminum dihalide are used a solid, rubbery material is produced having characteristics of ethylene-propylene rubber. This rubbery material is useful in the manufacture of tires, wire coating, footwear and other industrial products.

The homogeneous catalysts of this invention can be deposited upon a suitable support or carrier and used in the olefin reaction, preferably where the olefin feed is in the vapor phase. Catalyst supports include solid, inorganic or organic materials conventionally used as catalyst supports or carriers such as silica, alumina, silica-alumina, titania, boria, zeolites, ion exchange resins, solid polymers containing functional groups such as those prepared by the polymerization of 4-vinylpyridine, vinyl dimethylphosphine, and the like.

The support can be impregnated with the homogeneous catalyst by wetting the support with a solution of the catalyst in a solvent which is then evaporated.

Among solvents suitable are relatively low-boiling organic solvents such as pentane, methylene chloride, cyclohexane, and the like. The amount of homogeneous catalyst added to the support will be from 0.1 to about 30 weight percent of the total of the catalyst and support. If the support is to be activated by calcination, it is usually activated prior to the impregnation step.

Impregnation and evaporation conditions in preparing the catalyst are conventional, being carried out at temperatures up to about 150° C. Operating conditions in carrying out the olefin reaction are the same for the supported and the nonsupported homogeneous catalyst systems.

That which is claimed is:

1. A metal complex represented by the formula $[(L)_a(NO)_b M_c Z_d]_x$ wherein M is niobium or vanadium; each Z is a halogen, CN, SCN, OCN, or $SnCl_3$ radical; each (L) is a ligand represented by the formula $R_3QO$, O, $[(RCO)_2CH{+}]$, $R{-}S{-}R$, $R^5(CN)_b$, $R^5(COO{+})_b$, $(R^5COR^2COO{+})$, or $$\overset{R^3}{\underset{\smile}{\phantom{x}}}S;$$

wherein a, b, c, and d, are integers wherein a is 1–6, b is 1–2, c is 1–4, d is 0–6, and the number of Z, (L), and NO groups in the complex is not greater than the number required for the metal to achieve the closed shell electronic configuration of the next higher atomic number inert gas; x is the number of the polymeric state of the complex; Q is phosphorus, arsenic, or antimony; R is an aromatic or saturated aliphatic hydrocarbon radical having up to 20 carbon atoms per molecule; $R^2$ is a divalent R radical; $R^3$ is a divalent saturated or ethylenically unsaturated aliphatic radical having from 4 to 10 carbon atoms; and $R^5$ is an aromatic, saturated aliphatic, or ethylenically unsaturated aliphatic radical having up to 30 carbon atoms.

2. The metal complex of claim 1 wherein said M is vanadium.

3. The complex of claim 1 wherein said metal complex is NOBr-treated (ethylenedinitrile)$O_2V_2$(acetate)$_4$, NOCl-treated VO(lactate)$_2$, NOI-treated (2,4-pentanedionate)$_2O_V$, NOCl-treated (2,4-pentanedionate)$_2$ (triphenylphosphine oxide)V, NOBr-treated (1-phenyl-1,3-butanedionate)$_2$V, NO-treated (2,4-pentanedionate)OVCl$_2$, NO-treated (acetate)$_2$VCl$_4$, NOCl-treated (2,4-pentanedionate)$_3$V, or NOBr-treated (1-phenyl-1,3-butanedionate)$_3$V.

4. The metal complex of claim 1 wherein M is niobium.

5. The metal complex of claim 1 further including a diluent in which said complex is at least partially soluble.

6. The metal complex of claim 5 wherein said diluent is carbon tetrachloride, methylene chloride, benzene, cyclohexane, xylene, isooctane, or chlorobenzene.

7. The metal complex of claim 1 wherein said complexing agent is triphenylphosphine oxide, tribenzylphosphine oxide, trimethylarsine oxide, tributylstibine oxide, tricyclopentylarsine oxide, tricyclohexylphosphine oxide, trieicosylstibine oxide, tridecylphosphine oxide, tri-p-tolylphosphine oxide, acetic acid, propionic acid, butanoic acid, 2-methylpropionic acid, pentanoic acid, hexanoic acid, octanoic acid, dodecanoic acid, hexadecanoic acid, octadecanoic acid, triacontanoic acid, benzoic acid, phenylacetic acid, oxalic acid, malonic acid, acetoacetic acid, benzoylacetic acid, β-acetylpropionic acid, δ-acetobutyric acid, acetonitrile, butyronitrile, 1,2-cyclohexylenedinitrile, ethylenedinitrile, acrylonitrile, 2,4-pentanedione, 1,3-diphenyl-1,3-pentanedione, 3,5-heptanedione, 4-cyclohexyl-2,4-butanedione, ethylsulfide, phenylsulfide, methylethyl sulfide, thiophene, or tetrahydrothiophene.

8. A metal complex represented by $[(L)_a(NO)_b M_c Z_d]_x$ consisting essentially of a product formed by the admixture, under complex forming conditions, of (A) a niobium or vanadium compound which is the niobium or vanadium halide, oxyhalide, cyanide, thiocyanate, cyanate, trichlorostannate, or salt of a hydrocarbon organic acid having up to 30 carbon atoms per molecule, (B) NO or a nitrosyl halide, and (C) a complexing agent capable of complexing with said niobium or vanadium, wherein in said metal complex M is niobium or vanadium, Z is halogen, CN, SCN, OCN, or $SnCl_3$ radical, L is a ligand represented by the formula O, $[(RCO)_2CH{+}]$, $R{-}S{-}R$, $R^5(CN)_b$, $R^5(COO{+})_b$, $(R^5COR^2COO{+})$, or $$\overset{R^3}{\underset{\smile}{\phantom{x}}}S;$$

a, b, c, and d are integers wherein a is 1–6, b is 1–2, c is 1–4, d is 0–6, and x is a number representative of the polymeric state of the complex, R is an aromatic or saturated aliphatic hydrocarbon radical of up to 20 carbon atoms $R^2$ is a divalent R radical, $R^3$ is a divalent saturated or ethylenically unsaturated aliphatic radical of 4 to 10 carbon atoms, and $R^5$ is an aromatic, saturated aliphatic, or ethylenically unsaturated aliphatic radical of up to 30 carbon atoms, and wherein said (C) complexing agent is represented by the formula: $RCOCH_2COR$; $R^5(CN)_b$; $R{-}S{-}R$;

$$\overset{R^3}{\underset{\smile}{\phantom{x}}}S;$$

acids of the formula $R^5(COOH)_b$; or ketoacids of the formula $R^5COR^2COOH$, employing a molar proportion of vanadium or niobium compound to complexing agent in the range of about 0.1:1 to 10:1.

9. The metal complex of claim 8 wherein said vanadium compound is $VBr_3$, $VCl_2$, $VCl_3$, $VCl_4$, $VF_3$, $VF_5$, VOCl, VOBr, $VOBr_2$, $VOBr_3$, $VO_2Cl$, $VOCl_2$ or $VOCl_3$.

10. The metal complex of claim 8 wherein said niobium compound is $NbBr_5$, $NbCl_5$, $NbF_5$, $NbOBr_3$, or $NbOCl_3$.

11. The metal complex of claim 8 wherein said vanadium or niobium compound is niobium or vanadium halide or oxyhalide.

12. The metal complex of claim 8 wherein said niobium or vanadium compound is $NbCl_5$, said complexing agent is benzoic acid, and said NO or nitrosyl halide is said NO.

13. A process for preparing a metal complex which comprises admixing under complexing conditions and in complex forming ratios (A) a niobium or vanadium compound which is the niobium or vanadium halide, oxyhalide, cyanide, thiocyanate, cyanate, trichlorostannate, or salt of a hydrocarbon acid having up to 30 carbon atoms per molecule,
with (B) NO or a nitrosyl halide,
and (C) with at least one complexing agent capable of complexing said niobium or vanadium wherein said ratio of said niobium or vanadium compound to said complexing agent is in the range of about 0.1:1 to about 10:1, and
wherein said complexing agent is represented by the formula:

$RCOCH_2COR$: $R^5(CN)_b$; $R-S-R$;

$\overset{R^3}{\underset{\smile}{S}}$;

acids of the formula $R^5(COOH)_b$; or ketoacids of the formula $R^5COR^2COOH$; wherein R is an aromatic or saturated aliphatic hydrocarbon radical having up to 20 carbon atoms; $R^2$ is a divalent R radical, $R^3$ is a divalent saturated or ethylenically unsaturated aliphatic radical having 4 to 10 carbon atoms, $R^5$ is an aromatic, saturated aliphatic, or ethylenically unsaturated aliphatic radical having up to 30 carbon atoms, and $b$ is an integer of 1 or 2.

14. The process for preparing the metal complex according to claim 13 wherein said niobium or vanadium compound is said halide or oxyhalide.

15. The process according to claim 13 wherein said niobium or vanadium compound is said vanadium compound, and is selected from the group consisting of $VBr_3$, $VCl_2$, $VCl_3$, $VCl_4$, $VF_3$, $VF_5$, $VOCl$, $VOBr$, $VOBr_2$, $VOBr_3$, $VO_2Cl$, $VOCl_2$, and $VOCl_3$.

16. The process according to claim 13 wherein said niobium or vanadium compound is said niobium compound and is selected from the group consisting of $NbBr_5$, $NbCl_5$, $NbF_5$, $NbOBr_3$, or $NbOCl_3$.

17. The metal complex prepared by the process of reacting (a) niobium chloride with (b) NO and (c) benzoic acid, under complex-forming conditions employing a molar ratio of about 1:2 niobium chloride:benzoic acid.

18. The metal complex which is NO-treated benzoic acid $NbCl_5$, NO-treated (tetrahydrothiophene) $NbBr_5$, or NO-treated (tetrahydrothiophene) $NbCl_5$.

* * * * *

UNITED STATES PATENT AND TRADEMARK OFFICE
CERTIFICATE OF CORRECTION

PATENT NO. : 4,126,577

DATED : November 21, 1978

INVENTOR(S) : William B. Hughes et al

It is certified that error appears in the above–identified patent and that said Letters Patent are hereby corrected as shown below:

Col. 11, claim 3, line 4, "dionate)$_2$O$_v$" should read --- dionate)$_2$O$_2$V ---.

Signed and Sealed this

Tenth Day of April 1979

[SEAL]

Attest:

RUTH C. MASON
*Attesting Officer*

DONALD W. BANNER
*Commissioner of Patents and Trademarks*